United States Patent [19]

Popitz

[11] Patent Number: 4,918,774
[45] Date of Patent: Apr. 24, 1990

[54] MEDICAL SUPPORT PILLOW

[75] Inventor: Michael D. Popitz, Boston, Mass.

[73] Assignee: Brigham and Women's Hospital, Boston, Mass.

[21] Appl. No.: 394,642

[22] Filed: Aug. 16, 1989

[51] Int. Cl.⁵ .............................................. A47G 9/00
[52] U.S. Cl. ............................................. 5/441; 5/434
[58] Field of Search .................. 5/441, 434, 436, 437; D6/601

[56] References Cited

U.S. PATENT DOCUMENTS

| | | |
|---|---|---|
| 2,521,780 | 9/1950 | Dodd . |
| 2,896,227 | 7/1959 | Reed ...................................... 5/441 |
| 2,940,087 | 6/1960 | Kiefer . |
| 3,694,831 | 10/1972 | Treace . |
| 4,218,792 | 8/1980 | Kogan .................................... 5/436 |
| 4,259,757 | 4/1981 | Watson .................................. 5/433 |
| 4,320,543 | 3/1989 | Dixon .................................... 5/434 |
| 4,424,599 | 1/1984 | Hannouche ........................... 5/434 |
| 4,494,261 | 1/1985 | Morrow ................................. 5/434 |
| 4,754,513 | 7/1988 | Rinz ....................................... 5/434 |
| 4,773,107 | 9/1988 | Josefek .................................. 5/434 |
| 4,805,603 | 2/1989 | Cumberland ......................... 5/441 |
| 4,829,614 | 5/1989 | Harper .................................. 5/441 |

OTHER PUBLICATIONS

Principles of Airway Management; p. 128, by Brendan P. Finvcane, ©1988.

Primary Examiner—Alexander Grosz
Attorney, Agent, or Firm—Saidman, Sterne, Kessler & Goldstein

[57] ABSTRACT

The present invention provides a medical support pillow for automatically aligning the oropharyngeal, laryngeal and tracheal axes of the human head for airway management. The support pillow includes a head support and a neck support which are dimensioned to automatically align the airway axes when the head and neck are positioned thereupon.

20 Claims, 2 Drawing Sheets

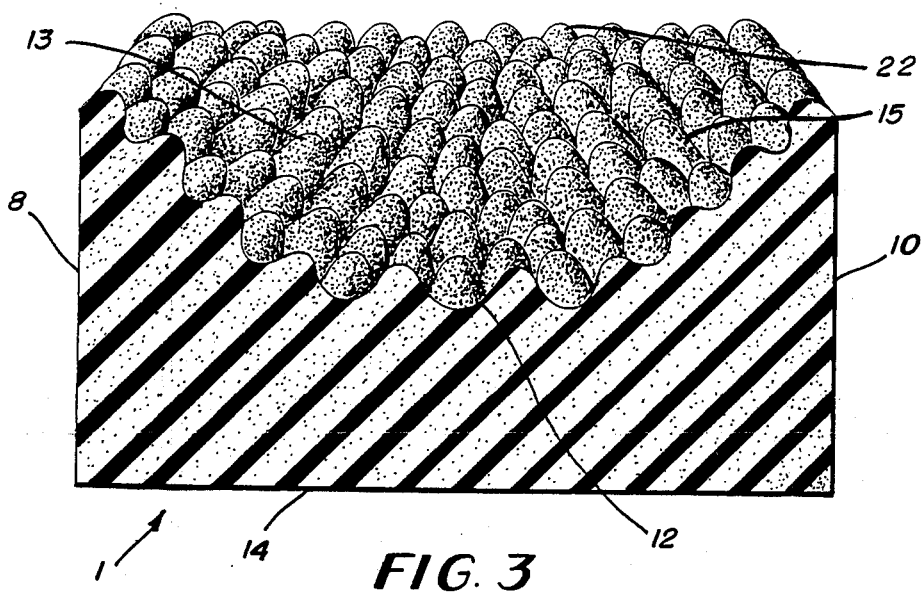
FIG. 3
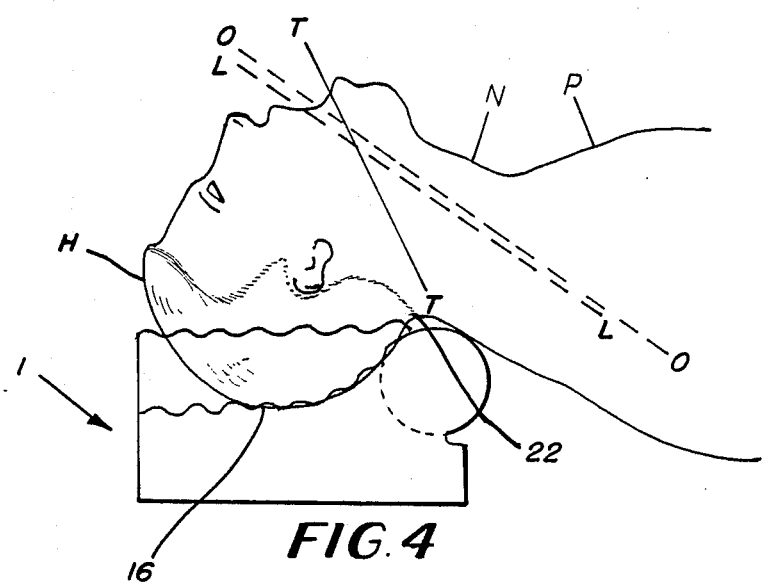
FIG. 4
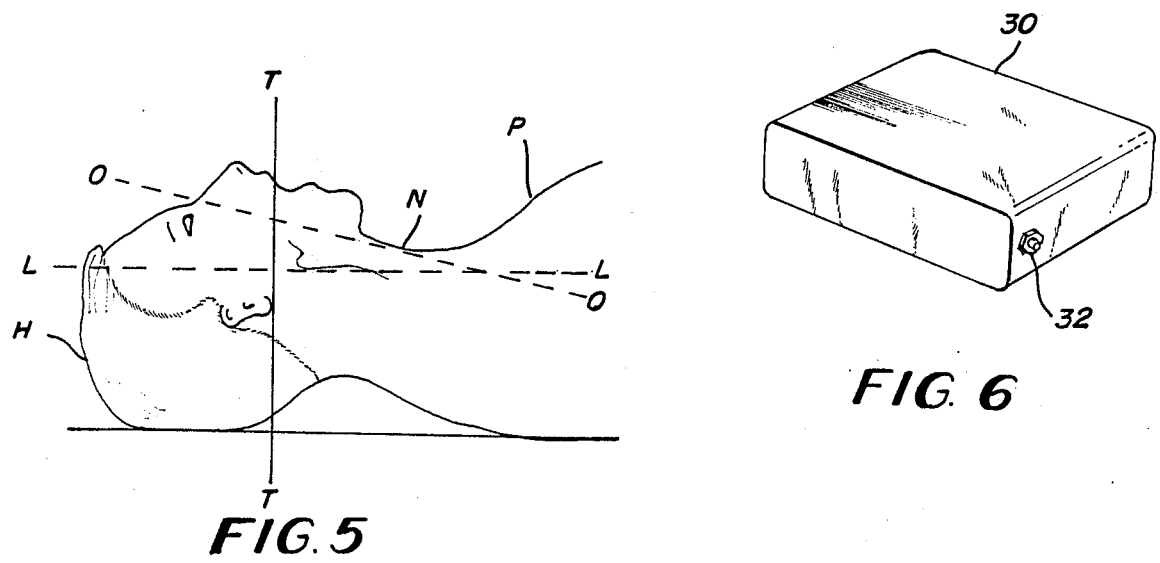
FIG. 5
FIG. 6

MEDICAL SUPPORT PILLOW

FIELD OF THE INVENTION

The present invention relates to medical support cushions, and more particularly to a medical support pillow for aligning the oropharyngeal, laryngeal and tracheal axes of the head for airway management.

BACKGROUND OF THE INVENTION

Many medical procedures used today require some type of patient airway management. Examples of such procedures include general anesthesia/intubation, mask anesthesia, regional anesthesia/sedation with $O_2$ supplementation, and semi-surgical and radiologic procedures. Many patients die unnecessarily due to an inability to ventilate or difficulty encountered during intubation.

Successful airway management requires aligning the oropharyngeal, laryngeal and tracheal axes such that the passageway from the incisor teeth to the glottis is most nearly a straight line. This technique requires training and experience to make it safe, effective and atraumatic. Elevating the head about 10 cm with pads or towels under the occiput (shoulders remaining on the table), flexing the neck and extending the head at the alanto-occipital joint, either by tilting the head backward with one hand or by pulling up on the mandible (a bone in the lower jaw) with the fingers of one hand, serve to align these axes most nearly into a straight line. This posture is described as the "sniffing position." However, without proper positioning of the head and neck of the patient, it is difficult for even the very skilled anesthetist to intubate.

In most operating rooms, the patient's head is rested upon a folded blanket. Currently, to accomplish intubation, the person attending the patient must use his hands to properly position the patient's head in the sniffing position. Other methods commonly utilized include placing a pillow or towel under the shoulders of the patient or allowing the patient's head to literally hang over the end of the bed or operating table. Although these positions may be thought to open the airway, they will not facilitate airway management because no attempt is made to align the oropharyngeal, laryngeal and tracheal axes. Not only do these methods result in a higher incidence of morbidity (i.e., damaged teeth or traumatized vocal cords) and mortality (i.e., from esophageal intubation), they rely on the skills of the attending person. However, even those skilled in this field may fail to properly align the patient's head and neck every time the procedure is used.

Another problem encountered in the operating room occurs when the patient is having mask anesthesia, or a regional technique with IV sedation. The airway becomes obstructed due to the relaxation of the muscular structures of the oropharynx. This necessitates, for example, manually maneuvering the patient's jaw for the remainder of the procedure, resulting in an unnecessarily fatigued anesthetist, and less efficient ventilation.

To eliminate these problems, support cushions for use during surgical procedures have been proposed. One example is found in the Watson patent (U.S. Pat. No. 4,259,757) which discloses a support cushion for maintaining a patient's head in proper position during endotracheal intubation, for example, as well as during other medical procedures. A 7° inclination in the cushion allows the three airway axes of the patient to be aligned when the head is correctly positioned within a depression provided in the cushion. While this cushion is capable of supporting the head in the sniffing position once the axes are aligned, it does not aid in aligning the axes. Therefore, the Watson cushion still requires a skilled attendant to manipulate the head and neck of the patient into the proper position. Furthermore, this cushion does not provide neck support for the patient, a technique which aids in aligning the airway axes. Thus, although some support is provided for the head by the Watson cushion, the risk of patient morbidity and mortality remains ever present.

SUMMARY OF THE INVENTION

It is with these problems in mind that the present invention was developed. Unlike the previously used methods of airway management, the present invention does not rely on the skill of the attendant. Rather, by merely placing the patient's head and neck on the pillow, the patient's airway axes are aligned and the airway is spontaneously opened. Additionally, in the event of respiratory failure, the respiratory therapist, utilizing the support pillow, can ventilate the patient much easier until the skilled intubator arrives. It is also contemplated that the support pillow may be used as an anti-snoring device or a sleep apnea aid.

In accordance with the purposes of the present invention, as embodied and described herein, the present invention is a support pillow for supporting the head and neck of a human, comprising a base for supporting the head, a neck support for supporting the neck and a head support having a center head supporting surface which slopes downwardly from the neck support toward a head end. The head support also includes a left head supporting surface which slopes downwardly from the left side toward an occiput contacting point and a right heading supporting surface which slopes downwardly from the right side toward the center head supporting surface. The head support and neck support are dimensioned to automatically align the oropharyngeal, the laryngeal, and the tracheal axes of a human when the head and neck are positioned upon the support pillow. The base of the support pillow may be generally square, and the neck support may be generally cylindrical. The neck support may extend from the left side of the base to the right side of the base.

Furthermore, the invention is a support for automatically aligning the oropharyngeal, laryngeal and tracheal axes of a human head and neck, comprising a support means for supporting the head and neck of the human, which includes a head support means for supporting the head and a neck support means for supporting the neck. The head support means includes a neck end, and the neck support means is positioned at the neck end of the head support means. The support means is dimensioned to automatically align the oropharyngeal, the laryngeal and the tracheal axes of the human head and neck when placed on the support means. The head support means may be generally rectangular, and the neck support means may be generally cylindrical. The head support means may also include a head supporting surface which slopes downwardly from the neck end to a forward end. The head supporting surface may also slope downwardly from a left side toward a right side and may slope downwardly from the right side toward the left side. The neck support means may be coextensive with the neck end.

The support pillow may be constructed of nonallergenic material, such as urethane foam, and may have a textured surface to alleviate pressure points on the head and neck. In the preferred embodiment, the distance between the head supporting surface at the occiput contacting point and the bottom surface may be approximately 3 to 3 ½ inches. The support pillow may also comprise an internal bladder which may be selectively inflated by the introduction of fluid into the bladder. When in use, the bladder allows alteration of the contour of the head supporting surface.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which:

FIG. 3 is a transverse cross-sectional view taken along lines 3—3 of FIG. 1.

FIG. 6 shows an inflatable bladder which may be used with an alternative embodiment of the support pillow of FIG. 1.

DETAILED DESCRIPTION OF THE DRAWINGS

Figure 1:
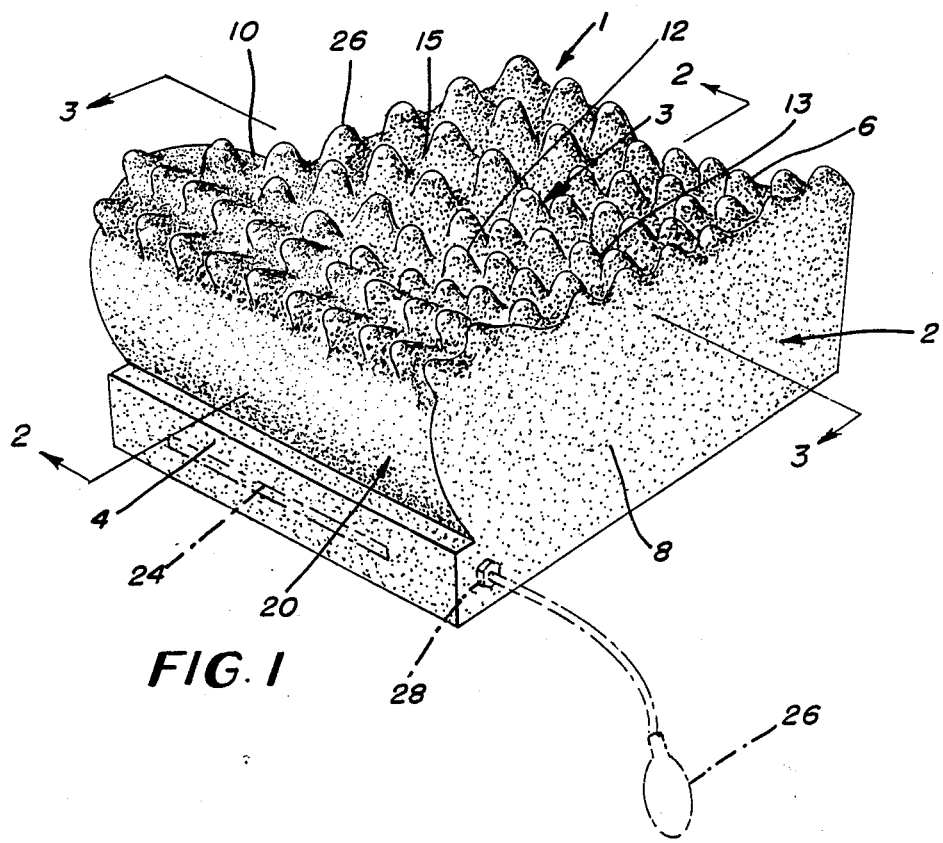
FIG. 1 is a perspective view of the support pillow of the present invention.

The support pillow of the present invention for automatically aligning the airway axes of a patient is shown generally at 1 in FIG. 1. The support pillow 1 comprises a base, shown generally at 2; a head support, shown generally at 3, for supporting the head of the patient; and a neck support shown generally at 20, for supporting the neck of the patient. Base 2 and supports 3 and 20 may be unitary or they may be individual components joined by any suitable means to form support pillow 1. Each of these components will be described in more detail below.

Base 2 is preferably generally square, although other geometric configurations are possible, and supports head support 3 and neck support 20. Base 2 includes a left side 8; a right side 10 (FIG. 3); a neck end 4; a head end 6; and a bottom surface 14. Head support 3 which is supported on base 2 comprises three head supporting surfaces: a center head supporting surface 12, a left head supporting surface 13 and a right head supporting surface 15. Head support 3 extends from head end 6 of base 2 to neck support 20; and from left side 8 to right side 10. Center head supporting surface 12 slopes downwardly from neck support 20 toward head end 6. Left head supporting surface 13 slopes downwardly from left side 8 toward center head supporting surface 12; and right head supporting surface 15 slopes downwardly from right side 10 to center head supporting surface 12. Surfaces 12, 13 and 15 form a trough-shaped recess for receiving the back and sides of the head of the patient.

Turning now to neck support 20, which preferably has a generally cylindrical configuration, it includes a neck supporting surface 22 (FIG. 2) which provides the necessary support for the neck of a patient. Neck support 20 is positioned on base 2 at neck end 4 and extends from left side 8 to right side 10 of base 2. Neck support 20 forms a roll for supporting the neck of the patient in a flexed position as is required for proper airway management.

Figure 2:
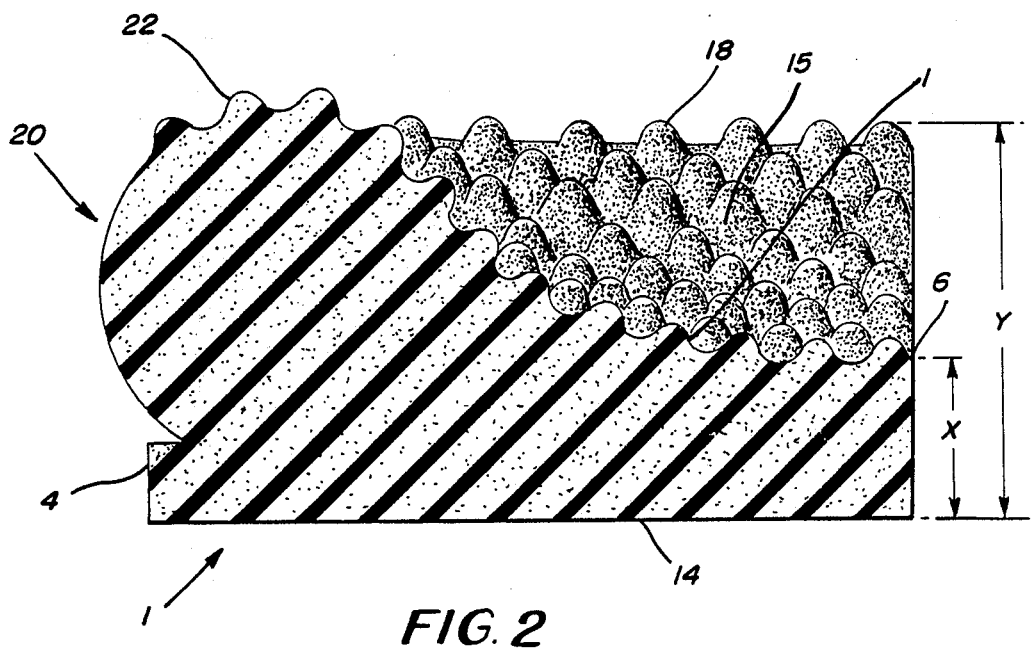
FIG. 2 is a longitudinal cross-sectional view taken along lines 2—2 of FIG. 1.

As best seen in FIG. 2, center head supporting surface 12 and bottom surface 14 define dimension X, which represents the distance from head supporting surface 12 to bottom surface 14 of base 2. Dimension Y, also shown in FIG. 2, represents the distance from the highest point 18 of one side, the right side 10, of right head supporting surface 15 to bottom surface 14. The distance from the highest point of left side 8 to left head supporting surface 13 to bottom surface 14 is also equal to Y.

Figure 4:
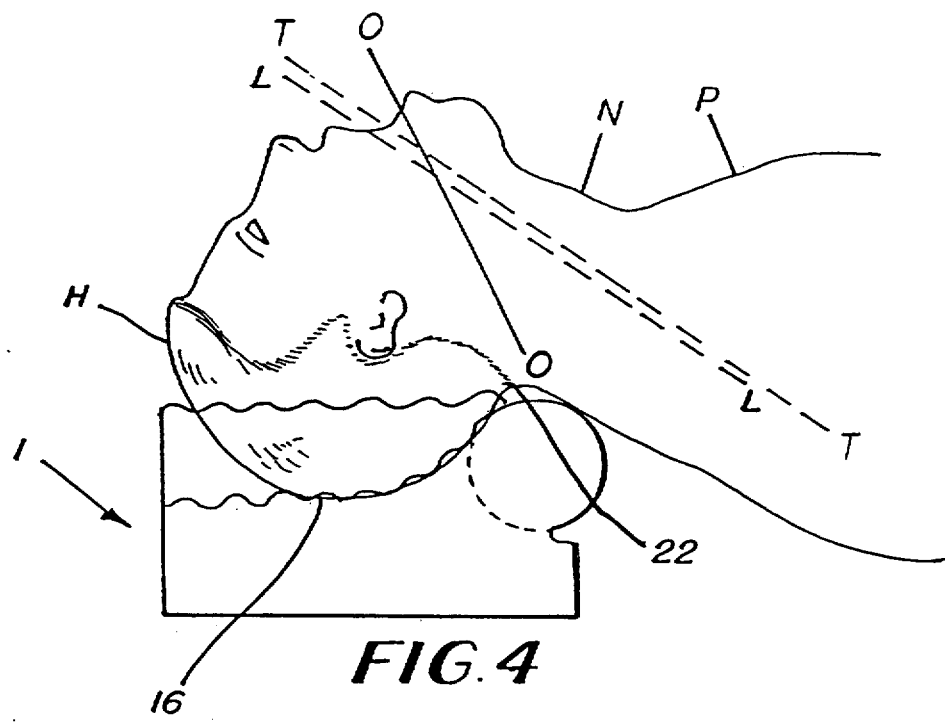
FIG. 4 depicts the support pillow in use, with a patient, showing the alignment of axes L, O and T for proper airway management.

As best seen in FIG. 1, neck supporting surface 22 lies in a plane higher than the lowest point of head supporting surface 12; while the highest point of left and right head supporting surfaces 13 and 15 lie in a plane that is substantially the same as the one in which neck supporting surface 22 lies. While the particular dimensions of X and Y will vary depending upon the size of the pillow (which in turn will vary according to the particular size of the patient to be serviced by the pillow), in the preferred embodiment, X is approximately 3 to 3 ½ inches, and Y is approximately 5 to 6 inches. It has been found that by dimensioning the support pillow in this manner, the oropharyngeal 0, laryngeal L and tracheal L axes of a patient are automatically aligned when the head and neck of the patient are positioned on support pillow 1, as shown in FIG. 4 and described below. However, other dimensions are possible so long as they achieve the same function as the present invention. Similarly, the degree at which head supporting surfaces 12, 13 and 15 slope may be varied, so long as proper alignment of the airway axes is maintained.

FIG. 4 depicts support pillow 1 in use, during which base 2 rests on bottom surface 14. A patient P is shown with his head positioned in support pillow 1; the neck N is supported on neck supporting surface 22, the back and sides of the head H are supported on surfaces 12, 13 and 15. Axis 0—0 represents the oropharyngeal axis; axis L-L represents a laryngeal axis; and axis T-T represents the tracheal axis of patient P. Due to the arrangement of sloping surfaces 13 and 15, support pillow 1 allows access to the patient's face, while minimizing lateral movement of the head. That is, when the head is positioned on the pillow, sloping left and right head supporting surfaces 13 and 15 cradle the sides of the head and prevent the head from rolling to either side of the pillow.

As a result of the orientation of sloping surfaces 12, 13 and 15 and of neck supporting surface 22, when the head H and neck N of patient P are positioned in support pillow 1 as shown in FIG. 4, axes 0, L and T become properly aligned for airway management. Because surface 12 slopes downwardly from neck support 20, the neck N is flexed upwards and the head H is angled downwardly, to automatically align the head H and neck N of the patient into the sniffing position, by aligning axes L, O and T. When the patient head H is properly positioned on pillow 1, the occiput 16 of the patient skull directly contacts head supporting surface 12.

Figure 5:
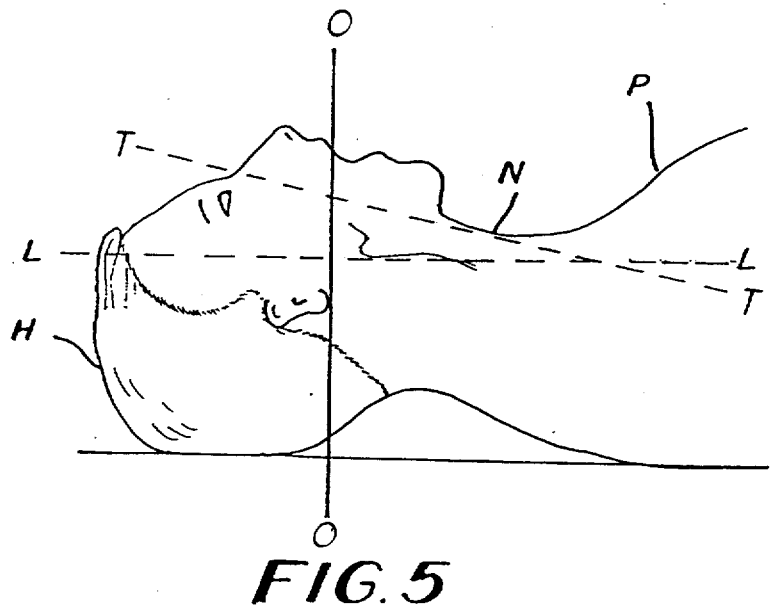
FIG. 5 depicts the arrangement of axes L, 0 and T of a patient in the natural, unsupported position.

In contrast to FIG. 4, FIG. 5 depicts the head H and neck N of patient P in the natural, unsupported position. It is clear from FIG. 5 that axes 0, L and T are improperly aligned, and thus patient P is not in a position suitable for safe and efficient airway management.

Support pillow 1 is preferably made of a suitable non-allergenic material of sufficient density to support the head, while also providing resilient cushioning. One example of a suitable material is urethane foam. The material for constructing support pillow 1 is also preferably anti-flammable. Furthermore, the entire support pillow 1 may be disposable, or a disposable slip cover might be used to prevent the spread of contagious disease.

In addition, head supporting surfaces 12, 13 and 15 and neck supporting surface 22 of support pillow 1 as shown, have a textured surface to alleviate pressure points on the patient's head and neck caused by prolonged use. One example of a suitable material for providing a textured surface is a high density, convoluted foam available from E.R. Carpenter Company, Richmond, Virginia.

FIG. 6 depicts a fluid, preferably air, inflatable bladder 30 which may be incorporated as an optional accessory to support pillow 1. Bladder 30 may be inserted into a slot 24 formed in pillow 1 (shown in phantom in FIG. 1), which connects to an interior chamber (not shown). Bladder 30 is utilized in conjunction with an inflation pump 26 (also shown in phantom in FIG. 1). Pump 26 is connected to pillow 1 by a valve 28. Pump 26 is similar to a blood pressure cuff pump. However, any suitable means for adjustably inflating bladder 30 may be used in place of pump 26. A second valve 32 (FIG. 6) connects internal bladder 30 to inflation pump 26 when bladder 30 is placed within the interior chamber in pillow 1 through slot 24.

Bladder 30 allows an even finer adjustment of the patient's head neck into the sniffing position by a skilled anesthetist and can be selectively inflated to alter the contour of the head supporting surfaces 12, 13 and 15, and neck supporting surface 22. Furthermore, use of internal bladder 30 allows a more complete viewing of the patient's vocal cords, thereby preventing injury thereto when medical devices are inserted into the patient's throat. Moreover, internal bladder 30, when used, can compensate for decreased extension of a patient's atlanto-occipital joint, a common problem with arthritic patients, and thereby allow for increased neck flexion.

Support pillow 1, while extremely useful in medical procedures, is not intended to be limited thereto. In particular, other uses of support pillow 1 include a device to prevent snoring (an anti-snoring device) and an aid for sleep apnea, which are known to be aided by alignment of the oropharyngeal, laryngeal and tracheal axes of the human head and neck.

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations in changes may be made by those skilled in the art without departing from the spirit of the invention. Accordingly, the foregoing detailed description should be considered exemplary in nature and not limited to the scope and spirit of the invention as set forth in the attached claims.

What is claimed is:

1. A support pillow for supporting and maintaining the head and neck of a human in the sniffing position in which the neck is flexed upwards and the head is angled downwardly to achieve alignment of the airway axes, comprising:
    a base, said base having an opposing neck end and head end, an opposing left side and right side, and a bottom surface;
    a neck support, for supporting the neck, said neck support positioned at said neck end of said base;
    a head support for supporting the head, said head support including a center head supporting surface which slopes downwardly from said neck support toward said head end;
    said head support further including a left head supporting surface which slopes downwardly from said left side toward said center head supporting surface;
    said head support further including a right head supporting surface which slopes downwardly from said right side toward said center head supporting surface; and
    said head support and said neck support being dimensioned relative to each other to automatically align and maintain alignment of the oropharyngeal, the laryngeal and the tracheal airway axes of the human in the sniffing position when said head and neck are positioned upon said support pillow.

2. A support pillow as set forth in claim 1, wherein said base is generally square.

3. A support pillow as set forth in claim 1, wherein said neck support is generally cylindrical.

4. A support pillow as set forth in claim 1, wherein said neck support extends from said left side of said base to said right side of said base.

5. A support pillow as set forth in claim 1, wherein said support pillow is constructed of non-allergenic material.

6. A support pillow as set forth in claim 5; wherein said material is urethane foam.

7. A support pillow as set forth in claim 5, wherein said material has a textured surface to alleviate pressure points on said head and neck.

8. A support pillow as set forth in claim 1, wherein the distance between said center head supporting and said bottom surface is approximately 3 to 3 ½ inches.

9. A support pillow as set forth in claim 1, further comprising:
    an internal bladder, said bladder adapted to be selectively inflated by the introduction of fluid into said bladder, wherein said bladder allows alteration of the contour of said head support and said neck support.

10. A support for automatically aligning and maintaining alignment of the oropharyngeal, the laryngeal and the tracheal axes of a human head and neck in the sniffing position in which the neck is flexed upwards and the head is angled downwardly, comprising:
    a support means for supporting the head and neck of the human, said support means including a base, a head support means for supporting said head and a neck support means for supporting said neck;
    said support means including a neck end;
    said neck support means positioned at said neck end of said support means;
    said head support means including a head supporting surface;
    said neck support means including a neck supporting surface, wherein the distance from said base to said neck supporting surface is greater than the distance from said base to said head supporting surface, such that said support is dimensioned to automatically align and maintain the oropharyngeal, the laryngeal and the tracheal axes of the human head and neck when placed on said support.

11. A support, as set forth in claim 10, wherein said head support means is generally square.

12. A support, as set forth in claim 10, wherein said neck support means is generally cylindrical.

13. A support, as set forth in claim 10, wherein said support further comprises:
   a head end, wherein said head support means extends from said neck end to said head end; and
   said head support means includes a head supporting surface which slopes downwardly from said neck end to said head end.

14. A support, as set forth in claim 13, wherein said support further comprises:
   a left side and an opposing right side;
   wherein said head supporting surface slopes downwardly from said left side toward said right side; and
   wherein said head supporting surface further slopes downwardly from said right side toward said left side.

15. A support, as set forth in claim 10, wherein said neck support means is coextensive with said neck end.

16. A support, as set forth in claim 10, wherein said support is constructed of non-allergenic material.

17. A support, as set forth in claim 16, wherein said material is urethane foam.

18. A support, as set forth in claim 16, wherein said material has a textured surface to alleviate pressure points on said head and neck.

19. A support, as set forth in claim 10, wherein said head support means further includes a bottom surface opposite said head supporting surface; and
   wherein the distance between a center of said head supporting surface and said bottom surface is approximately 3 to 3 ½ inches.

20. A support, as set forth in claim 10, wherein said support further comprises:
   an internal bladder, said bladder adapted to be selectively inflated by the introduction of fluid into said bladder, wherein said bladder allows alteration of the surface of said head support means and said neck support means.

* * * * *

UNITED STATES PATENT AND TRADEMARK OFFICE
CERTIFICATE OF CORRECTION

PATENT NO. : 4,918,774
DATED : April 24, 1990
INVENTOR(S) : Popitz

It is certified that error appears in the above-identified patent and that said Letters Patent is hereby corrected as shown below:

In the drawings, delete Figures 4 and 5 and substitute therefor corrected Figures 4 and 5 attached hereto.

Signed and Sealed this

Fifteenth Day of December, 1992

Attest:

DOUGLAS B. COMER

*Attesting Officer*   Acting Commissioner of Patents and Trademarks